United States Patent [19]

Hanaoka et al.

[11] Patent Number: 5,120,762

[45] Date of Patent: Jun. 9, 1992

[54] METHOD FOR PRODUCTION OF STABILIZED SODIUM ASCORBATE POWDER

[75] Inventors: Tadashi Hanaoka, Toyonaka; Sadao Jike, Hikari; Itsumasa Iwamoto, Kumage, all of Japan

[73] Assignee: Takeda Chemical Industries, Ltd., Osaka, Japan

[21] Appl. No.: 684,437

[22] Filed: Apr. 11, 1991

Related U.S. Application Data

[63] Continuation of Ser. No. 258,861, Oct. 17, 1988, abandoned.

[30] Foreign Application Priority Data

Oct. 19, 1987 [JP] Japan .................. 62-264690

[51] Int. Cl.$^5$ .............................................. A61K 31/34
[52] U.S. Cl. .................................... 514/474; 514/970
[58] Field of Search ............................... 514/474, 970

[56] References Cited

U.S. PATENT DOCUMENTS

| | | | |
|---|---|---|---|
| 2,442,461 | 6/1948 | Karrer | 167/81 |
| 3,116,204 | 12/1963 | Siegel et al. | 167/81 |
| 3,446,894 | 5/1969 | Magid | 424/176 |
| 3,773,930 | 11/1973 | Kasheed | 514/474 |
| 3,973,032 | 8/1976 | Leonard | 514/474 |

OTHER PUBLICATIONS

Chem. Abst., 70:31647r (1969), Kagami.
Chem. Abst, 69:59537h, (1968), Renault.

*Primary Examiner*—Frederick E. Waddell
*Assistant Examiner*—Zohreh A. Fay
*Attorney, Agent, or Firm*—Wenderoth, Lind & Ponack

[57] ABSTRACT

Ascorbic acid composition comprising a trace amount of an alkli metal compound or an alkaline earth metal compound is very stable with respect to coloring and does not acquire a yellow color even after along time storage.

The composition can be easily obtained by addition of only a trace amount of an additive.

3 Claims, No Drawings

METHOD FOR PRODUCTION OF STABILIZED SODIUM ASCORBATE POWDER

This application is a continuation of Application Ser. No. 07/258,861, filed Oct. 17, 1988, now abandoned.

This invention relates to a stabilized ascorbic acid composition which is not subject to changes such as coloring along with time and to the method for production of the powder.

Presently available formulations containing ascorbic acid or a salt thereof contain various stabilizers for prevention of deterioration. For example, the addition of sorbose or lactose for stabilization of tablets containing ascorbic acid (U.S. Pat. No. 3,446,894) and the addition of cystein or thiolactic acid for stabilization of aqueous solutions of calcium ascorbate (U.S. Pat. No. 2,442,461) have been proposed.

Ascorbic acid powder obtained by pulverization of crystalline ascorbic acid has problems of stability because it is subject to changes along with time in a normal atmosphere and acquires a yellow color more easily than the original crystals. To solve these problems, storage of the powder under an inert gas by sealing, and storage in the presence of a dehydrating agent have been tried.

As the result of the inventors' research on stabilization of ascorbic acid compositions, the inventors have found that the presence of only a trace amount of an alkali metal compound or an alkaline earth metal compound is enough for preparation of very stable ascorbic acid compositions.

This invention relates to (1) stabilized ascorbic acid compositions comprising an alkali metal compound or an alkaline earth metal compound in the amount of about 100 ppm or less, and (2) the method for production of stabilized ascorbic acid powder, which comprises pulverizing crystals of ascorbic acid in the presence of an alkali metal compound or an alkaline earth metal compound in the amount of about 100 ppm or less.

Several kinds of preparations, such as a powder, a granule, an infinitesinal grain, a tablet and so on, can be made of the composition of this invention. Especially these compositions are very useful to prepare ascorbic acid powders.

Alkali metal compounds and alkaline earth metal compounds that can be used in this invention include alkali metal salts and alkaline earth metal salts of organic acids, alkali metal salts and alkaline earth metal salts of inorganic acids, and hydroxides of alkali metals and alkaline earth metals. Alkali metals constituting these salts and hydroxides include potassium and sodium, and such alkaline earth metals include calcium and magnesium.

Alkali metal salts and alkaline earth metal salts of organic acids include salts of aromatic carboxylic acids such as sodium benzoate, salts of saturated and unsaturated aliphatic carboxylic acids such as sodium acetate, sodium succinate, potassium sorbate, sodium sorbate, sodium fumarate, sodium propionate, and calcium propionate, salts of oxycarboxylic acids such as sodium citrate, calcium citrate, calcium gluconate, potassium hydrogen tartrate, sodium hydrogen tartrate, sodium lactate, calcium lactate, sodium malate, calcium pantothenate, and sodium panthothenate, salts of amino acids such as sodium L-glutamate, and salts of enolic acids such as sodium erythorbate, sodium L-ascorbate, and calcium L-ascorbate.

Alkali metal salts and alkaline earth metal salts of inorganic acids include salts of hydrochloric acid, sulfuric acid, nitric acid, carbonic acid, and phosphoric acid, such as sodium chloride, calcium chloride, magnesium chloride, sodium nitrate, potassium nitrate, sodium sulfate, calcium sulfate, magnesium sulfate, potassium carbonate, sodium carbonate, calcium carbonate, magnesium carbonate, sodium thiosulfate, potassium pyrophosphate, sodium pyrophosphate, potassium phosphate, sodium phosphate, and calcium phosphate.

Hydroxides of alkali metals and alkaline earth metals include sodium hydroxide and calcium hydroxide.

Among the alkali metal compounds and alkaline earth metal compounds (called simply metal compounds hereinafter), edible alkali metal salts and alkaline earth metal salts of organic acids, especially enolic acids, and sodium hydroxide are preferable.

The amount of the metal compound contained in the composition is as small as 100 ppm or less; even 0.5-50 ppm of the compound is sufficient for stabilization. The more preferable amount of the compound is about 1-10 ppm.

Mixing of one of the metal compounds described above with the ascorbic acid powder is performed for example by pulverization of crystals of ascorbic acid in the presence of the metal compound. This method will yield a very stable ascorbic acid composition. The methods to incorporate a metal compound into crystals of ascorbic acid include: (a) uniform addition of the metal compound to the crystals to make a mixture, (b) sprinkling by some way, such as by the use of a solution of the metal compound (e.g. aqueous solution, solution in alcohol such as methanol, solution in ketone such as methylethylketone) in place of methanol for usually washing the crystals over the crystals, followed by removal of the solvent by filtration with suction or by centrifugation and drying to give crystals to which the metal compound is attached, and (c) crystallization of ascorbic acid in a solution comprising the metal compound to give crystals in which the metal compound has been incorporated. Among these, the method (b) is particularly desirable. The amount of the metal compound to be contained in the ascorbic acid composition can be controlled at will by selection of the amount to be added in the method (a), concentration of the metal compound in the solution and amount of the solvent to be removed in the method (b), and the concentration in the solution in the method (c). The concentration of a metal compound in the solution in the method (b) is desirably about 0.01-5 w/v%.

In the next step the crystals of ascorbic acid in which a metal compound is present are dried by heating under reduced pressure or in a stream of air and pulverized. Pulverization of crystals of ascorbic acid is performed with a conventional pulverizer, such as hammer mill and jet mill type pulverizer.

A stabilized ascorbic acid powder can be obtained by pulverization into fine powder of 100 mesh pass (JIS Z8801) or less with such a pulverizer, and such a fine powder can be stabilized by the method of this invention.

Ascorbic acid compositions comprising a trace amount of an alkali metal compound or an alkaline earth metal compound in this invention is very stable with respect to coloring and does not acquire a yellow color even after a long time storage. With the method of this invention a stabilized ascorbic acid composition can be easily obtained by addition of only a trace amount of an additive; thus this method is industrially very useful. de This invention will be illustrated more concretely in the following examples.

EXAMPLE 1

An aqueous slurry of ascorbic acid wherein ascorbic acid is present in the form of crystals was filtrated with suction to give 200 g of wet crystals. Over these crystals on the filter flask, 200 ml of 0.02 w/v% solution of sodium hydroxide in methanol was sprinkled at room temperature (20°-25° C). The solution was then removed by filtration with suction. The crystals wherein sodium hydroxide was present were dried under reduced pressure, and pulverized with a hammer mill (manufactured by Fuji Powdal Co., Ltd.), to give 190 g of ascorbic acid powder of 200 mesh pass. The powder contained about 4 ppm of sodium.

EXAMPLE 2

Except that 200 ml of 0.1 w/v% solution of sodium ascorbate in water-methanol (water/methanol-1/100) was used in place of 200 ml of the solution of sodium hydroxide in methanol in Example 1, a similar treatment to that in Example 1 gave 190 g of ascorbic acid powder of 100 mesh pass. The powder contained about 30 ppm of sodium ascorbate.

EXAMPLE 3

Except that 200 ml of 0.1 w/v% solution of sodium benzoate in methanol was used in place of 200 ml of the solution of sodium hydroxide in methanol in Example 1, a similar treatment to that in Example 1 gave 185 g of ascorbic acid powder of 100 mesh pass. The powder contained about 35 ppm of sodium benzoate.

EXAMPLE 4

Except that 150 ml of 0.02 w/v% cold aqueous solution of calcium hydroxide was used in place of 200 ml of the solution of sodium hydroxide in methanol in Example 1, a similar treatment to that in Example 1 gave 180 g of ascorbic acid powder of 100 mesh pass. The powder contained about 3 ppm of calcium.

EXAMPLE 5

Except that 150 ml of 0.01 w/v% cold aqueous solution of calcium ascorbate was used in place of 200 ml of the solution of sodium hydroxide in methanol in Example 1, a similar treatment to that in Example 1 gave 180 g of ascorbic acid powder of 100 mesh pass. The powder contained about 35 ppm of calcium ascorbate.

TEST EXAMPLE

Ten g of each one of the preparations of ascorbic acid powder obtained in Examples 1 to 5 was separately dissolved in pure water to give 50 ml of an aqueous solution, and the absorbance at 400 nm of each of the solutions was determined. The powder obtained by pulverization of crystals of ascorbic acid with a pulverizer was used as the control. The six powder preparations were tested again in the same way after 3-year-storage in well-closed containers. The results of the tests are summarized in the following table.

| | UV absorbance (400 nm) 5 cm cell | |
| --- | --- | --- |
| Example No. | powder just after preparation | powder after 3-year-storage |
| 1 | 0.016 | 0.043 |
| 2 | 0.016 | 0.044 |
| 3 | 0.015 | 0.054 |
| 4 | 0.015 | 0.059 |
| 5 | 0.015 | 0.051 |
| control | 0.015 | 0.261 |

Absorbance at 400 nm is an indication of yellow coloring of the powder, and thus it has been proved that the ascorbic acid powder preparations of this invention are very stable, hardly acquiring a yellow color.

Each of powders obtained in Example 1-5 is measured for the concentration of chloric ion, which is one of the contaminations in the powder. It cannot be detected by the method of the conventional potentiometric titration.

Each of the powders contains not more than 2.0 ppm of chloric ion.

What we claim is:

1. A powder composition consisting essentially of ascorbic acid and 0.5 to 50 ppm of at least one compound selected from the group consisting of an alkali metal salt of ascorbic acid, an alkaline earth metal salt of ascorbic acid, a hydroxide of an alkali metal and a hydroxide of an alkaline earth metal.

2. A composition according to claim 1 wherein the said compound is an alkali metal salt of ascorbic acid or an alkaline earth metal salt of ascorbic acid.

3. A method for the production of stabilized ascorbic acid powder, which comprises pulverizing crystals of ascorbic acid in the presence of at least one compound selected from the group consisting of an alkali metal salt of ascorbic acid, an alkaline earth metal salt of ascorbic acid, a hydroxide of an alkali metal and a hydroxide or an alkaline earth metal, the amount of said compound being from 0.5 to 50 ppm.

* * * * *